United States Patent [19]
Ladd et al.

[11] 3,983,245
[45] Sept. 28, 1976

[54] CERTAIN 4-(3-AZACYCLOALKOXY OR AZACYCLOALKYLMETHOXY)BENZOYL-BENZOFURANS OR BENZOTHIOPHENES

[75] Inventors: David L. Ladd, Penllyn; Stephen T. Ross, Berwyn, both of Pa.

[73] Assignee: SmithKline Corporation, Philadelphia, Pa.

[22] Filed: Feb. 6, 1975

[21] Appl. No.: 547,528

[52] U.S. Cl. .......................... 424/285; 260/293.57; 260/293.58; 260/326.5 D; 260/326.5 SA; 260/330.5; 260/346.2 R; 424/267; 424/274; 424/275
[51] Int. Cl.² ............... A61K 31/34; C07D 405/12; C07D 409/12
[58] Field of Search ............... 260/346.2 R, 293.58, 260/326.5 D, 326.5 SA, 293.57, 330.5; 424/267, 274, 285, 275

[56] References Cited
UNITED STATES PATENTS

| | | | |
|---|---|---|---|
| 3,248,401 | 4/1966 | Tondeur et al. | 260/346.2 R |
| 3,394,125 | 7/1968 | Crenshaw | 260/326.5 |
| 3,637,659 | 1/1972 | Plostnieks | 260/293.58 |

OTHER PUBLICATIONS

Derwent Abst. No. 71954S — Belgian Pat. 766392 June 22, 1970.
Derwent Abst. No. 81178T — Belgian Pat. 784260 June 25, 1971.
Derwent Abst. No. 21007V — Belgian Pat. 804550 Sept. 19, 1972.
Derwent Abst. No. 66559V German Pat. 2,408,476 Mar. 2, 1973.

*Primary Examiner*—Natalie Trousof
*Assistant Examiner*—Bernard Dentz
*Attorney, Agent, or Firm*—Janice E. Williams; Joan S. Keps; William H. Edgerton

[57] ABSTRACT

The compounds of this invention are substituted benzofurans and benzothiophenes having pharmacological activity. In particular, these compounds have coronary vasodilator activity and are useful in the treatment of angina pectoris.

11 Claims, No Drawings

CERTAIN 4-(3-AZACYCLOALKOXY OR AZACYCLOALKYLMETHOXY)BENZOYLBENZOFURANS OR BENZOTHIOPHENES

This invention relates to new substituted benzofurans and benzothiophenes which have useful pharmacological activity. More specifically, the compounds of this invention have coronary vasodilator activity and are useful in the treatment of angina pectoris. In addition, these compounds may be useful as hypotensive agents.

The compounds of this invention are represented by the following structural formula:

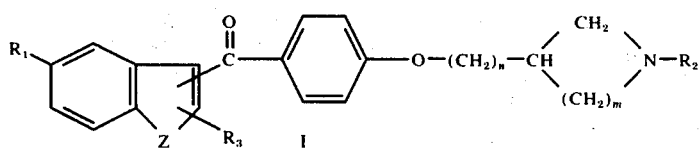

or a pharmaceutically acceptable acid addition salt thereof, in which:

$R_1$ is hydrogen, chloro, bromo, trifluoromethyl or lower alkyl;

$R_2$ is straight or branched chain alkyl of from one to six carbon atoms;

$R_3$ is lower alkyl or phenyl$(CH_2)_p$ where $p$ is 0 or 1 and the phenyl moiety is unsubstituted or substituted in the para-position with lower alkyl, lower alkoxy, halogen or trifluoromethyl;

$m$ is 1 to 4;

$n$ is 0 or 1; and

Z is oxygen or sulfur.

As used herein, the terms "lower alkyl" and "lower alkoxy" denote groups having from one to four carbon atoms; "halo" refers to chloro, bromo and fluoro.

Advantageous compounds of this invention are represented by formula I in which Z is oxygen.

Most advantageous are the compounds of formula I in which $R_3$ is in the 2-position of the benzofuran nucleus and Z is oxygen.

Particularly advantageous are the compounds where $R_1$ is hydrogen; $R_3$ is phenyl or phenyl substituted in the para-position with lower alkyl, lower alkoxy, halogen or trifluoromethyl and in the 2-position of the benzofuran nucleus and Z is oxygen.

Preferred compounds of this invention are represented by formula I in which $R_1$ is hydrogen, $R_3$ is phenyl in the 2-position of the benzofuran nucleus and Z is oxygen.

Most preferred are the compounds of formula I in which $R_1$ is hydrogen, $R_2$ is branched chain alkyl of from three to six carbon atoms, $R_3$ is phenyl in the 2-position of the benzofuran nucleus and Z is oxygen.

A particularly preferred compound of this invention is 3-[4-(N-t-butyl-3-azetidinomethoxy)benzoyl]-2-phenylbenzofuran which has the following structural formula:

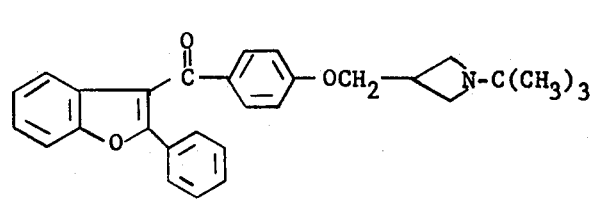

The compounds of formula I are prepared as shown in the following scheme:

SCHEME A

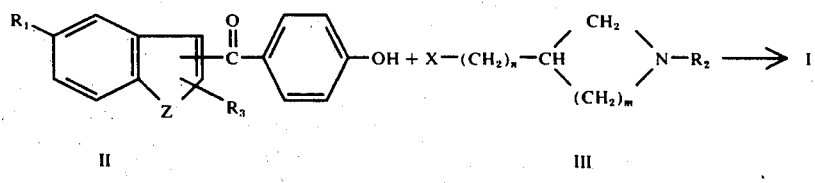

where $R_1$, $R_2$, $R_3$, $m$, $n$ and Z are defined as above and X is halogen, preferably chloro or bromo.

According to the above procedure, reaction of a hydroxyphenyl benzofuranyl ketone or hydroxyphenyl benzothiophenyl ketone of formula II with an (N-alkyl)heterocyclic amine halide of formula III in the presence of a base such as potassium carbonate, sodium methoxide or sodium hydride in a solvent such as methanol, ethanol, toluene or dimethylsulfoxide or, preferably, potassium carbonate in a solvent such as acetone, 2-butanone or 3-pentanone at a temperature of about 25°C. to the reflux temperature of the solvent for from about 6 to about 24 hours gives compounds of formula I.

Alternatively, the compounds of formula 1 are prepared as shown in Scheme B:

SCHEME B

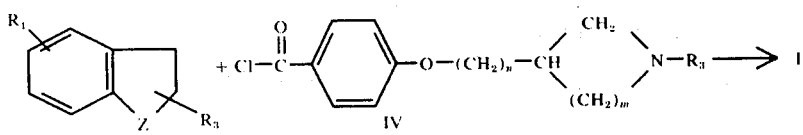

where $R_1$, $R_2$, $R_3$, $m$, $n$ and $Z$ are defined as above.

Thus, a benzofuran or benzothiophene nucleus is acylated with a substituted (N-alkyl)heterocyclic aminoalkoxybenzoyl chloride (IV) by standard procedures, for example in the presence of stannic chloride or aluminum chloride in a solvent such as methylene chloride, nitrobenzene or carbon disulfide at a temperature from about 0°C. to ambient temperature (ca. 25°). This method of preparing the compounds of formula I is particularly advantageous when $Z$ is sulfur and/or $R_3$ contains an alkoxy group.

The products of formula I are isolated and purified as such by standard techniques including solvent extraction, crystallization and chromatographic methods or as the corresponding acid addition salts which are also objects of this invention. The salts are formed with organic and inorganic acids according to methods known to the art. Thus, a solution of the amine in ether, chloroform or an alcohol such as methanol or ethanol is treated with a solution of an organic or inorganic acid in an aqueous miscible solvent, such as acetone or ethanol, with isolation of the salt by concentration and cooling or in an aqueous immiscible solvent, such as ether, with the desired salt separating directly. Exemplary of such organic salts are those with maleic, fumaric, benzoic, ascorbic, pamoic, succinic, hexamic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids as well as with the 8-halotheophyllines, for example, 8-bromotheophylline. Exemplary of such inorganic salts are those with hydrochloric, hydrobromic, sulfuric, sulfamic, phosphoric and nitric acids. Of course, these salts may also be prepared by the classical method of double decomposition of appropriate salts which is well known to the art. The salts may be purified by the standard methods described above.

The hydroxyphenyl benzofuranyl ketone and hydroxyphenyl benzothiophenyl ketone starting materials of Scheme A are either known to the art or are prepared as outlined below:

SCHEME C

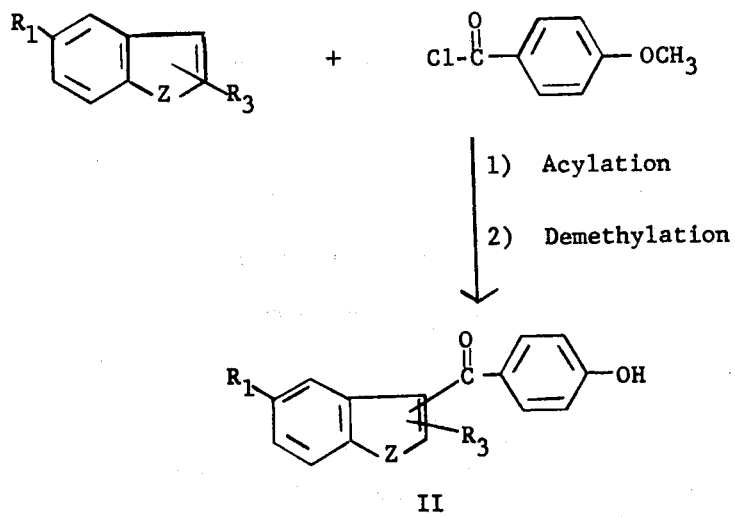

where $R_1$, $R_3$, and $Z$ are defined as above.

According to Scheme C, a methoxybenzoyl chloride is used to acylate a benzofuran or benzothiophene nucleus by standard procedures, for example in the presence of stannic chloride or aluminum chloride in a solvent such as methylene chloride, nitrobenzene or carbon disulfide. The methoxyphenyl benzofuranyl ketones and methoxyphenyl benzothiophenyl ketones are demethylated by known methods, for example by use of pyridine hydrochloride or boron tribromide. These and other methods are described by Buu-Hoi et al., *J. Chem. Soc.* 3693 (1955), 625 (1957), 2593 (1957), 173 (1964) and in Japanese Pat. No. 2482/64.

Alternatively, the hydroxyphenyl benzofuranyl ketone starting materials having $R_3$ in the 2-position of the benzofuran nucleus are prepared by addition of a methoxyphenyl magnesium halide to a 3-cyanobenzofuran followed by hydrolysis and subsequent demethylation as previously described.

The benzofuran starting materials in Schemes B and C are either known to the art or are prepared by one of the general methods for the synthesis of benzofurans described by Buu-Hoi et al., *J. Chem. Soc.* 3693 (1955), 625 (1957), 2593 (1957) and 173 (1964); Tanaka, *J. Amer. Chem. Soc.* 73:872 (1951); Bisagni et al., *J. Chem. Soc.* 3688 (1955); Grinev et al., *Zhur. Obshchei Khim.* 27:1087 (1957); Castro et al., *J. Org. Chem.* 28:3313 (1963), 31:4071 (1966); Rodd, *Chemistry of Carbon Compounds* Vol. IV-A, 168–191; Mustafa, *The Chemistry of Heterocyclic Compounds Vol. 29, Benzufurans* and French Pat. No. 1,537,206. Representative methods for preparing these starting materials are exemplified hereinafter.

The benzothiophene starting materials of Schemes B and C are known to the art or are prepared using a thiosalicylic acid and an α-bromophenyl or α-bromobenzyl acetic acid as starting materials according to the procedure described by Kucharczyk and Horak, *Collect. Czech. Chem. Commun.* 33:92 (1968).

The hydroxyphenyl benzofuranyl ketone starting materials of Scheme A in which $R_3$ is in the 3-position of the benzufuran nucleus are also prepared as follows:

SCHEME D

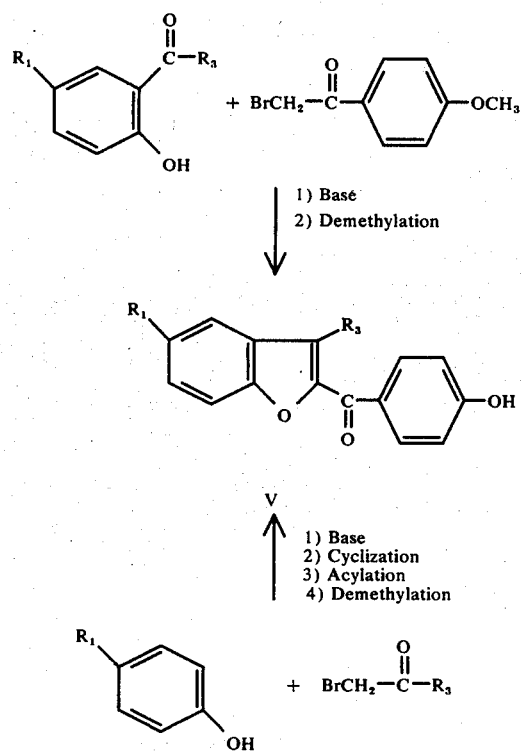

where $R_1$ and $R_3$ are defined as above.

Reaction of an o-hydroxyphenyl ketone with a substituted α-bromoacetophenone in the presence of a base, for example potassium carbonate, followed by dimethylation as described above gives the hydroxyphenyl benzofuranyl ketones of formula V.

In addition, the compounds of formula V are prepared as shown above by reaction of a substituted phenol with an α-bromoacetophenone of the formula

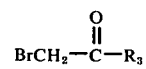

in the presence of a base such as potassium carbonate in a solvent such as acetone followed by cyclization of the intermediate thus formed, for example with polyphosphoric acid, and subsequent acylation and demethylation of the resulting 3-substituted benzofuran as described hereinabove.

The (N-alkyl)heterocyclic amine halides of formula III are either known or are prepared by reduction of an (N-alkyl)heterocyclic amine carboxylic acid to the corresponding hydroxy compound, for example with lithium aluminum hydride, followed by conversion of the hydroxy compound to the halide, III, by standard methods, such as by refluxing in aqueous hydrogen bromide or by reaction with triphenylphosphine in carbon tetrachloride.

The substituted (N-alkyl)heterocyclic aminoalkoxybenzoyl chlorides of formula IV are prepared by reaction of a substituted benzoic acid ester with an (N-alkyl)heterocyclic amine halide of formula III followed by ester hydrolysis and conversion of the acid to an acid chloride according to standard procedures.

The acid chloride acylating agents are either known to the art or are prepared by standard methods, for example by treatment of the corresponding acids with thionyl chloride or phosphorus pentachloride.

The coronary vasodilator activity and hypotensive effects of the compounds represented by formula I are demonstrated in dogs by an increase in coronary blood flow with concomitant decrease of mean arterial blood pressure upon intravenous administration of doses of from about 0.63 mg./kg. to about 10.0 mg./kg. These parameters are measured as follows:

Adult mongrel dogs (13–16 kg.) are pretreated with 2 mg./kg. s.c. of morphine sulfate followed in one hour by intravenous administration of 1–1.5 ml./kg. of an aqueous solution containing 1.5% chloralose and 20% urethane. Supplemental doses of morphine and chloralose-urethane are given to maintain an adequate and uniform depth of anesthesia.

A carotid artery is catheterized and connected to a Sanborn pressure transducer to measure arterial blood pressure. A femoral vein is also catheterized for administering a solution of the test compound or its salt and supplemental anesthesia. A left thoractomy is made at the fourth or fifth intercostal space, the lung is displaced, the pericardium is opened and the left circumflex coronary artery is isolated for measurement of coronary blood flow, a "snare" being placed around the artery distally to obtain zero flow. Coronary blood flow is measured with a Statham electromagnetic flowmeter and Flo-Probe.

In addition, the particularly preferred compound of formula I, which is 3-[4-(N-t-butyl-3-azetodinomethoxy)-benzoyl]-2-phenylbenzofuran, also inhibits or attenuates the chronotropic effect of isoproterenol-induced tachycardia upon administration to dogs at doses of from about 0.63 mg./kg. to about 10 mg./kg. i.v. Abad et al. [*Acta Pharmacol. et Toxicol.* 25:85 (1967)] have correlated the inhibition of isoproterenol-induced tachycardia to utility as an anti-anginal agent.

Pharmaceutical compositions having coronary vasodilator activity comprising a pharmaceutical carrier and a compound of formula I and methods of producing coronary vasodilation by administering these compounds are also objects of this invention.

The pharmacologically active compounds of this invention may be administered orally or parenterally in an amount to produce the desired activity.

Preferably the compounds are administered in conventional dosage unit forms prepared by combining an appropriate dose of the compound with standard pharmaceutical carriers. The dosage units will contain the active ingredient in an amount of from about 100 mg. to about 600 mg., preferably 150 mg. to 300 mg. per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or an aqueous or nonaqueous liquid suspension.

The pharmaceutical compositions are prepared by conventional techniques involving procedures such as mixing, granulating and compressing when necessary or variously mixing and dissolving the ingredients as appropriate to the desired composition.

The method of producing coronary vasodilator activity in accordance with this invention comprises administering internally to an animal an effective amount of a compound of formula I. The compound will preferably be administered in a dosage unit form as described above orally or parenterally, the oral route being preferred. Advantageously equal doses will be administered one to two times daily with the daily dosage regimen being from about 200 mg. to about 1200 mg., preferably from about 300 mg. to about 600 mg. When the method described above is carried out, coronary vasodilator activity is produced.

One skilled in the art will recognize that in determining the amounts of the compound needed to produce the desired pharmacological effect without toxic side effects, the activity of the compound as well as the size of the host animal must be considered.

The following examples illustrate the invention but are not to be construed as limiting the scope thereof. Temperatures are in degrees Centigrade unless otherwise stated.

When formed, acid adition salts may be converted to the corresponding free amines by treating a solution of the salt in a solvent such as water, a chloroform-water or a benzene-water mixture with a base such as 10% aqueous sodium hydroxide, sodium carbonate or sodium bicarbonate until basic followed by extraction of the amine into benzene or chloroform. Salts other than hydrochlorides may be converted to the corresponding hydrochloric acid salts by passing a solution of the salt in methanol or ethanol through a chloride ion exchange column.

EXAMPLE 1

3[4-(N-t-Butyl-3-azetidinoxy)benzoyl]-2-phenylbenzofuran

To a cooled (ice bath) mixture of 7.81 g. (0.040 mol.) of 2-phenylbenzofuran and 7.0 g. (0.041 mol.) of p-anisoyl chloride in 100 ml. of methylene chloride is added dropwise 28.7 g. (0.11 mol.) of stannic chloride. The reaction mixture is allowed to warm to ambient temperature, then stirred for two hours. Water is slowly added to the mixture and it is stirred an additional 30 minutes. The layers are separated and the organic phase is washed with water until the washings are neutral, dried (MgSO$_4$) and concentrated to give 3-(4-methoxybenzoyl)-2-phenylbenzofuran.

3-(4-Methoxybenzoyl)-2-phenylbenzofuran (16.4 g., 0.05 mol.) is combined with 50 g. of freshly distilled pyridine hydrochloride and the mixture is refluxed one hour. The hot mixture is poured with stirring onto an ice-dilute hyrochloric acid mixture and the precipitate is collected to give 3-(4-hydroxybenzoyl)-2-phenylbenzofuran.

A mixture of 1.0 g. (3.18 mmol.) of 3-(4-hydroxybenzoyl)-2-phenylbenzofuran, 0.47 g. (3.18 mmol.) of N-t-butyl-3-chloroacetidine, 0.18 g. of potassium hydroxide and 35 ml. of absolute ethanol was heated at reflux for six hours. The mixture was filtered and concentrated. The residue was dissolved in ether and the solution was filtered, washed with 2% aqueous sodium hydroxide solution and water, dried (MgSO$_4$) and evaporated to dryness to give the title compound.

An ethereal solution of hydrogen chloride was added to a solution of the title compound in ether and the resulting oil was triturated with ether to give the title compound as its hydrochloride salt.

EXAMPLE 2

2-n-Butyl-3-[4-(N-t-butyl-3-azetidinoxy)benzoyl]benzofuran

A mixture of 3.98 g. (13.5 mmol.) of 2-n-butyl-3-(4-hydroxybenzoyl)benzofuran, 2.0 g. (13.5 mmol.) of N-t-butyl-3-chloroazetidine and 0.54 g. of sodium hydroxide in 75 ml. of ethanol was refluxed for five hours. The reaction mixture was cooled, filtered and 125 ml. of 10% aqueous sodium hydroxide solution was added. The mixture was extracted three times with chloroform, the combined extracts were evaporated to dryness and the residue was chromatographed on alumina with chloroform as eluant to give the title compound.

The title compound was converted to the corresponding hydrochloride salt as described in Example 1.

EXAMPLE 3

3-[4-(N-t-Butyl-3-azetidinomethoxy)benzoyl]-2-phenylbenzofuran

N-t-Butylazetidine-3-carboxylic acid (5.0 g., 0.318 mol.) was added portionwise to a slurry of 1.81 g. (0.0477 mol.) of lithium aluminum hydride in 135 ml. of tetrahydrofuran. The mixture was refluxed for 12 hours, cooled and 2 ml. of water and 2 ml. of 15% aqueous sodium hydroxide were added followed by an additional 6 ml. of water. The mixture was filtered and the precipitate was washed with ether. The filtrate and washings were combined and evaporated to dryness to give N-t-butyl-3-hydroxymethylazetidine, b.p. 124°–127° (27 mm.).

A mixture of 3.0 g. (0.209 mol.) of N-t-butyl-3-hydroxymethylazetidine, 6.0 g. (0.0229 mol.) of triphenylphosphine and 50 ml. of carbon tetrachloride was refluxed for 48 hours. The mixture was cooled, filtered and the filtrate was extracted three times with 10% aqueous sulfuric acid. The combined extracts were basicified by addition of solid sodium carbonate and the basic solution was extracted with ether. The extract was dried (MgSO$_4$), evaporated to dryness and the residue distilled to give N-t-butyl-3-chloromethylazetidine, b.p. 90°–96° (27 mm.).

A mixture of 6.3 g. (0.020 mol.) of 3-(4-hydroxybenzoyl)-2-phenylbenzofuran, 3.15 g. (0.0195 mol.) of N-t-butyl-3-chloromethylazetidine and 1.01 g. (0.024 mol.) of 57% sodium hydride in mineral oil in 160 ml. of dimethylsulfoxide was heated at 110°–120° for 21 hours under a nitrogen atmosphere. The reaction mixture was poured into water and the aqueous solution was extracted three times with ether. The combined extracts were washed with 5% aqueous sodium hydroxide and water, dried (MgSO$_4$) and evaporated to dryness to give the title compound.

The title compound was converted to the corresponding hydrochloride salt as described in Example 1, m.p. 181°–183°.

EXAMPLE 4

3-[4-(N-Ethyl-3-pyrrolidinomethoxy)benzoyl]-2-phenylbenzofuran

A mixture of 5.0 g. (0.0388 mol.) of N-ethyl-3-hydroxymethylpyrrolidine and 50 ml. of 48% hydrogen bromide was refluxed for 17 hours. The reaction mixture was cooled, made basic by addition of solid sodium carbonate and extracted twice with methylene chloride. The combined extracts were dried (MgSO$_4$) and evaporated to dryness to give 3-bromomethyl-N-ethylpyrrolidine.

A mixture of 2.0 g. (6.36 mmol.) of 3-(4-hydroxybenzoyl)-2-phenylbenzofuran, 1.22 g. (6.36 mmol.) of 3-bromomethyl-N-ethylpyrrolidine and 3.52 g. of anhydrous potassium carbonate in 100 ml. of diethyl ketone was refluxed for 23 hours. The reaction mixture was filtered and evaporated to dryness and the residue was dissolved in ether. The ether solution was filtered, washed with 10% aqueous sodium hydroxide and water, dried (MgSO$_4$) and evaporated to dryness to give the title compound.

The title compound was converted to the corresponding hydrochloride salt as described in the procedure of Example 1, m.p. 168°–170°.

EXAMPLE 5

3-[4-(N-Ethyl-3-piperidinomethoxy)benzoyl]-2-phenylbenzofuran

A mixture of 5.0 g. (0.0349 mol.) of N-ethyl-3-hydroxymethylpiperidine and 52 ml. of 48% hydrogen bromide was refluxed for six hours then cooled and evaporated to dryness. The residue was made basic by addition of 5% aqueous sodium carbonate and extracted with methylene chloride. The methylene chloride solution was dried (MgSO$_4$) and evaporated to dryness to give 3-bromomethyl-N-ethylpiperidine.

A mixture of 2.0 g. (6.36 mmol.) of 3-(4-hydroxybenzoyl)-2-phenylbenzofuran, 1.31 g. (6.36 mmol.) of 3-bromomethyl-N-ethylpiperidine and 3.52 g. of anhydrous potassium carbonate in 100 ml. of diethyl ketone was refluxed for 19 hours. The cooled reaction mixture was filtered and the filtrate was evaporated to dryness to give the title compound.

The title compound was converted to the corresponding hydrochloride salt by the procedure described in Example 1.

EXAMPLE 6

3-[4-N-Ethyl-3-hexamethyleneiminomethoxy)benzoyl]-2-phenylbenzofuran

A mixture of 5.0 g. (0.039 mol.) of 3-hydroxymethylhexamethyleneimine and 20 ml. of acetic anhydride is warmed on a steam bath for one hour, then cooled and treated with an excess of aqueous sodium hydroxide. The mixture is extracted with ether and the extract is evaporated to dryness. The residue is dissolved in tetrahydrofuran, this solution is added to a solution of 2.0 g. (0.053 mol.) of lithium aluminum hydride in 50 ml. of tetrahydrofuran and the resulting mixture is refluxed for 12 hours. The mixture is cooled and ethanol, water and aqueous sodium hydroxide are added. The mixture is filtered and the filtrate is evaporated to dryness. The residue is dissolved in 50 ml. of 48% hydrobromic acid and the solution is refluxed for six hours, then evaporated to dryness. The residue is cooled, excess aqueous sodium carbonate is added and the solution is extracted with methylene chloride. The extract is evaporated to dryness to give 3-bromomethyl-N-ethylhexamethyleneimine.

Substitution of an equivalent amount of 3-bromomethyl-N-ethylhexamethyleneimine in the procedure of Example 5 for 3-bromomethyl-N-ethylpiperidine gives the title compound.

EXAMPLE 7

When 3-chloro-N-methylpiperidine is substituted in the procedure of Example 5 for 3-bromomethyl-N-ethylpiperidine, 3-[4-(N-methyl-3-piperidinoxy)benzoyl]-2-phenylbenzofuran is obtained.

Similarly, 3-[4-(N-propyl-3-piperidinoxy)benzoyl]-2-phenylbenzofuran is prepared by reaction of 3-chloro-N-propylbenzofuran and 3-(4-hydroxybenzoyl)-2-phenylbenzofuran according to the procedure of Example 5.

EXAMPLE 8

3-[4-N-t-Butyl-3-azetidinomethoxy)benzoyl]-2-methylbenzofuran

2-Methylbenzofuran (7.25 g., 0.055 mol.) was acylated with 15.7 g. (0.092 mol.) of p-anisoyl chloride according to the procedure described in Example 1 to give 3-(4-methoxybenzoyl)-2-methylbenzofuran. Demethylation as previously described gives 3-(4-hydroxybenzoyl)-2-methylbenzofuran.

Substitution of an equivalent amount of 3-(4-hydroxybenzoyl)-2-methylbenzofuran in the procedure of Example 3 for 3-(4-hydroxybenzoyl)-2-phenylbenzofuran gives the title compound.

EXAMPLE 9

When 2-ethyl-3-(4-hydroxybenzoyl)benzofuran or 3-ethyl-2-(4-hydroxybenzoyl)benzofuran is reacted with N-t-butyl-3-chloromethylazetidine as described in the procedure of Example 3, 3-[4-(N-t-butyl-3-azetidinomethoxy)-benzoyl]-2-ethylbenzofuran and 2-[4-(N-t-butyl-3-azetidinomethoxy)benzoyl]-3-ethylbenzofuran are obtained, respectively.

EXAMPLE 10

2-Benzyl-3-[4-(N-t-butyl-3-azetidinomethoxy)benzoyl]benzofuran

Acylation of 20.1 g. (0.096 mol.) of 2-benzylbenzofuran with 17.5 g. (0.103 mol.) of p-anisoyl chloride according to the procedure of Example 1 gave 2-benzyl-3-(4-methoxybenzoyl)benzofuran which was demethylated with pyridine hydrochloride to give 2-benzyl-3-(4-hydroxybenzoyl)benzofuran, m.p. 146°–149°.

Substitution of an equivalent amount of 2-benzyl-3-(4-hydroxybenzoyl)benzofuran in the procedure of Example 3 for 3-(4-hydroxybenzoyl)-2-phenylbenzofuran gives the title compound.

EXAMPLE 11

3-[4-N-t-Butyl-3-azetidinomethoxy)benzoyl]-2-(4-chlorobenzyl)benzofuran

To a solution of 15.3 g. (0.125 mol.) of salicylaldehyde in 100 ml. of acetone was added 7.0 g. (0.125 mol.) of potassium hydroxide dissolved in a minimum amount of water. α-Bromo-p-chloroacetophenone (29.16 g., 0.125 mol.) was added dropwise with stirring and cooling (ice bath). After addition, the reaction mixture was stirred at 25° for 12 hours. The precipitate was collected by filtration, washed with water and combined with the residue remaining after concentration of the filtrate to give 2-(4-chlorobenzoyl)-3-hydroxycoumaran which was immediately dehydrated in the presence of p-toluenesulfonic acid to yield 2-(4-chlorobenzoyl)benzofuran.

Hydrazine hydrate (28.0 g., 0.5 mol.) was added to a solution of 42.0 g. (0.16 mol.) of 2-(4-chlorobenzoyl)benzofuran in 400 ml. of ethanol and the reaction mixture was refluxed overnight. The solution was concentrated in vacuo, chloroform was added and the chloroform solution was washed with saturated aqueous sodium chloride, dried (MgSO$_4$) and concentrated to yield the corresponding hydrazone. The hydrazone was dissolved in 100 ml. of dry dimethyl sulfoxide and added dropwise over a four hour interval to a slurry of 36.4 g. (0.32 mol.) of potassium t-butoxide in 100 ml. of dry dimethyl sulfoxide. The reaction mixture was poured into 500 ml. of water and the aqueous solution was extracted with chloroform. The extracts were washed with water, dried (MgSO$_4$) and concentrated in vacuo to give 2-(4-chlorobenzyl)benzofuran which was purified by chromatography on silica gel with carbon tetrachloride as eluant.

Acylation of 2-(4-chlorobenzyl)benzofuran with p-anisoyl chloride was accomplished as described in Example 1. Demethylation with pyridine hydrochloride as previously described gave 2-(4-chlorobenzyl)-3-(4-hydroxybenzoyl)benzofuran.

Substitution of an equivalent amount of 2-(4-chlorobenzyl)-3-(4-hydroxybenzoyl)benzofuran in the procedure of Example 3 for 3-(4-hydroxybenzoyl)-2-phenylbenzofuran gives the title compound.

EXAMPLE 12

When 2-(4-chlorophenyl)benzofuran was acylated with p-anisoyl chloride as described in the procedure of Example 1 and the resulting 2-(4-chlorophenyl)-3-(4-methoxybenzoyl)benzofuran was demethylated with pyridine hydrochloride as previously described, 2-(4-chlorophenyl)-3-(4-hydroxybenzoyl)benzofuran was obtained.

Reaction of 2-(4-chlorophenyl)-3-(4-hydroxybenzoyl)benzofuran with N-t-butyl-3-chloromethylazetidine according to the procedure of Example 3 gives 3-[4-(N-t-butyl-3-azetidinomethoxy)benzoyl]-2-(4-chlorophenyl)benzofuran.

Similarly, acylation of 2-(4-tolyl)benzofuran with p-anisoyl chloride and subsequent demethylation with pyridine hydrochloride gave 2-(4-tolyl)-3-(4-hydroxybenzoyl)benzofuran.

Substitution of an equivalent amount of 2-(4-tolyl)-3-(4-hydroxybenzoyl)benzofuran in the procedure of Example 3 for 3-(4-hydroxybenzoyl)-2-phenylbenzofuran gives 3-[4-(N-t-butyl-3-azetidinomethoxy)benzoyl]-2-(4-tolyl)benzofuran.

EXAMPLE 13

2-[4-(N-t-Butyl-3-azetidinomethoxy)benzoyl]-3-phenylbenzofuran

Acylation of 3-phenylbenzofuran with p-anisoyl chloride over a four hour period as described in the procedure of Example 1 followed by demethylation of the 2-(4-methoxybenzoyl)-3-phenylbenzofuran thus formed as previously described gives 2-(4-hydroxybenzoyl)-3-phenylbenzofuran.

Substitution of an equivalent amount of 2-(4-hydroxybenzoyl)-3-phenylbenzofuran in the procedure of Example 3 for 3-(4-hydroxybenzoyl)-2-phenylbenzofuran gives the title compound.

EXAMPLE 14

2-[4-(N-t-Butyl-3-azetidinomethoxy)benzoyl]-3-(4-chlorophenyl)benzofuran

A mixture of 23.3 g. (0.1 mol.) of α-bromo-p-chloroacetophenone, 10.0 g. (0.1 mol.) of phenol and 14.5 g. (0.1 mol.) of potassium carbonate in 65 ml. of dry acetone is refluxed for 12 hours. The reaction mixture is cooled, poured into 500 ml. of water and the precipitate formed is collected by filtration and recrystallized from ethanol to give α-phenoxy-p-chloroacetophenone.

α-Phenoxy-p-chloroacetophenone (11.0 g., 0.045 mol.) is added to 90 g. of polyphosphoric acid preheated to 80° and the mixture is stirred for 12 hours. The reaction mixture is poured into 800 ml. of water and the aqueous mixture is extracted three times with ether. The combined extracts are washed with water, saturated aqueous sodium bicarbonate solution and saturated aqueous sodium chloride solution, dried (MgSO$_4$) and concentrated under reduced pressure to give 3-(4-chlorophenyl)benzofuran, m.p. 56°–57°.

Acylation of 3-(4-chlorophenyl)benzofuran with p-anisoyl chloride as described above followed by demethylation of the product formed with pyridine hydrochloride as previously described gives 3-(4-chlorophenyl)-2-(4-hydroxybenzoyl)benzofuran, m.p. 220°–221° (ethyl acetate).

Substitution of an equivalent amount of 3-(4-chlorophenyl)-2-(4-hydroxybenzoyl)benzofuran in the procedure of Example 3 for 3-(4-hydroxybenzoyl)-2-phenylbenzofuran gives the title compound.

EXAMPLE 15

2-[4-(N-t-Butyl-3-azetidinomethoxy)benzoyl]-3-methylbenzofuran

When an equivalent amount of o-hydroxyacetophenone is substituted in the procedure of Example 11 for salicylaldehyde and α-bromo-p-methoxyacetophenone is substituted for α-bromo-p-chloroacetophenone, there is ultimately obtained 3-methyl-2-(4-methoxybenzoyl)benzofuran. Demethylation of 3-methyl-2-(4-methoxybenzoyl)-benzofuran as described above gives 3-methyl-2-(4-hydroxybenzoyl)benzofuran.

Substitution of an equivalent amount of 3-methyl-2-(4-hydroxybenzoyl)benzofuran in the procedure of Example 3 for 3-(4-hydroxybenzoyl)-2-phenylbenzofuran gives the title compound.

EXAMPLE 16

2-n-Butyl-3-[4-(N-t-butyl-3-azetidinomethoxy)benzoyl]-5-chlorobenzofuran

A mixture of 27 g. (0.18 mol.) of 5-chlorobenzofuran, 28.5 g. (0.18 mol.) of butyric anhydride, 18 g. (0.20 mol.) of butyric acid and 5 g. (0.05 mol.) of phosphoric acid was refluxed for four hours then stirred at 25° for 12 hours. The reaction mixture was basicified with 10% aqueous sodium hydroxide, chloroform was added to the mixture and the layers were separated. The organic phase was washed with water, dried (MgSO$_4$) and concentrated in vacuo to give 2-butyryl-5-chlorobenzofuran.

A mixture of 31.5 g. (0.14 mol.) of 2-butyryl-5-chlorobenzofuran and 35 ml. of 98% hydrazine in 70 ml. of diethylene glycol was warmed for a few minutes on a steam bath. Then 23.3 g. of potassium hydroxide was added and the reaction mixture was refluxed for two hours. After cooling, water was added to the mixture and the resulting aqueous solution was extracted with benzene. The extract was washed with water, 10% aqueous hydrochloric acid and water, dried (MgSO$_4$) and concentrated in vacuo to yield 2-n-butyl-5-chlorobenzofuran, b.p. 70°–75° (10-15 mm.).

2-n-Butyl-5-chlorobenzofuran (9.5 g., 0.046 mol.) was acylated with 8 g. (0.047 mol.) of p-anisoyl chloride as described in the procedure of Example 1 to give 2-n-butyl-5-chloro-3-(4-methoxybenzoyl)benzofuran. Demethylation gives 2-n-butyl-5-chloro-3-(4-hydroxybenzoyl)benzofuran.

Substitution of an equivalent amount of 2-n-butyl-5-chloro-3-(4-hydroxybenzoyl)benzofuran in the procedure of Example 3 for 3-(4-hydroxybenzoyl)-2-phenylbenzofuran gives the title compound.

EXAMPLE 17

3-[4-(N-t-butyl-3-azetidinomethoxy)benzoyl]-5-chloro-2-phenylbenzofuran

A mixture of 14.2 g. (0.09 mol.) of cuprous phenylacetylide and 16.0 g. (0.08 mol.) of 2-bromo-4-chlorophenol in 130 ml. of pyridine was refluxed under a nitrogen atmosphere for 18 hours. The reaction mixture was cooled and poured into 600 ml. of water. The resulting precipitate was collected by filtration, washed with copious amounts of water and continuously extracted with ethanol for 12 hours. Removal of the ethanol in vacuo gave a residue which was chromatographed on an alumina dry column with hexane to give 5-chloro-2-phenylbenzofuran, m.p. 140°–143° (methanol).

Acylation of 5-chloro-2-phenylbenzofuran with p-anisoyl chloride was accomplished as described in the procedure of Example 1 to give 5-chloro-2-phenyl-3-(4-methoxybenzoyl)benzofuran which was then demethylated as described above to give 5-chloro-3-(4-hydroxybenzoyl)-2-phenylbenzofuran.

Substitution of an equivalent amount of 5-chloro-3-(4-hydroxybenzoyl)-2-phenylbenzofuran in the procedure of Example 3 for 3-(4-hydroxybenzoyl)-2-phenylbenzofuran gives the title compound.

EXAMPLE 18

Substitution of an equivalent amount of a benzofuran listed below:
5-bromobenzofuran
5-methylbenzofuran
5-ethylbenzofuran
in the procedure of Example 16 for 5-chlorobenzofuran followed by the synthetic steps of hydrazine reduction, acylation, demethylation and reaction of the hydroxybenzoyl intermediate with N-t-butyl-3-chloromethylazetidine as described therein gives the following substituted benzofurans as final products:
5-bromo-2-n-butyl-3-[4-(N-t-butyl-3-azetidinomethoxy)benzoyl]benzofuran
2-n-butyl-3-[4-(N-t-butyl-3-azetidinomethoxy)-benzoyl]-5-methylbenzofuran
2-n-butyl-3-[4-(N-t-butyl-3-azetidinomethoxy)-benzoyl]-5-ethylbenzofuran.

EXAMPLE 19

2-Benzyl-5-bromo-3-[4-(N-t-butyl-3-azetidiomethoxy)-benzoyl]benzofuran

A mixture of 35.5 g. (0.18 mol.) of 5-bromobenzofuran, 45.2 g. (0.18 mol.) of benzoic anhydride, 24.4 g. (0.20 mol.) of benzoic acid and 5 g. (0.05 mol.) of phosphoric acid is refluxed for four hours then stirred at 25° for 12 hours. The reaction mixture is basicified with 10% aqueous sodium hydroxide, chloroforom is added to the mixture and the layers are separated. The organic phase is washed with water, dried (MgSO$_4$) and concentrated under reduced pressure to give 2-benzoyl-5-bromobenzofuran.

A mixture of 42.2 g. (0.14 mol.) of 2-benzoyl-5-bromobenzofuran and 35 ml. of 98% hydrazine in 70 ml. of diethylene glycol is warmed for a few minutes on a steam bath. Then 23.3 g. of potassium hydroxide is added and the reaction mixture is refluxed for two hours. After cooling, water is added to the mixture and the resulting aqueous solution is extracted with benzene. The extract is washed with water, 10% aqueous hydrochloric acid and water, dried (MgSO$_4$) and concentrated to yield 2-benzyl-5-bromobenzofuran.

2-Benzyl-5-bromobenzofuran is acylated with p-anisoyl chloride as described above, the resulting 2-benzyl-5-bromo-3-(4-methoxybenzoyl)benzofuran is demethylated and the product thus formed is reacted with N-t-butyl-3-chloromethylazetidine as described in Example 3 to give the title compound.

EXAMPLE 20

3-[4-(N-t-Butyl-3-azetidinomethoxy)benzoyl]-5-chloro-2-ethylbenzofuran

When an equivalent amount of 5-chloro-2-ethylbenzofuran is substituted in the procedure of Example 1 for 2-phenylbenzofuran and the product thus formed is demethylated with pyridine hydrochloride then treated with N-t-butyl-3-chloromethylazetidine as previously described, the title compound is obtained.

EXAMPLE 21

3-[4-(N-t-Butyl-3-azetidinomethoxy)benzoyl]-2-(4-ethoxybenzyl)benzofuran 4-(N-t-Butyl-3-azetidinomethoxy)benzoic acid methyl ester is prepared by reaction of 4-hydroxybenzoic acid methyl ester, N-t-butyl-3-chloromethylazetidine and sodium hydride as described in the procedure of Example 3. Hydrolysis of 4-(N-t-butyl-3-azetidinomethoxy)benzoic acid methyl ester according to standard procedures gives 4-(N-t-butyl-3-azetidinomethoxy)benzoic acid which is converted to the corresponding acid chloride by reaction with thionyl chloride as previously described.

2-(p-Ethoxybenzyl)benzofuran is acylated with 4-(N-t-butyl-3-azetidinomethoxy)benzoyl chloride to give the title compound.

EXAMPLE 22

When 4-n-propylphenol or 4-trifluoromethylphenol is reacted with α-bromoacetophenone according to the procedure described in Example 14 and the resulting product is cyclized by heating with polyphosphoric acid at 80° as described therein, 3-phenyl-5-n-propylbenzofuran and 3-phenyl-5-trifluoromethylbenzofuran are obtained.

Acylation of 3-phenyl-5-n-propylbenzofuran or 3-phenyl-5-trifluoromethylbenzofuran with 4-(N-t-butyl-3-azetidinomethoxy)benzoyl chloride as previously described gives 2-[4-(N-t-butyl-3-azetidinomethoxy)benzoyl]-3-phenyl-5-n-propylbenzofuran and 2-[4-(N-t-butyl-3-azetidinomethoxy)benzoyl]-3-phenyl-5-trifluoromethylbenzofuran, respectively.

EXAMPLE 23

3-[4-(N-t-Butyl-3-azetidinomethoxy)benzoyl]-2-(4-ethylphenyl)benzofuran

A mixture of 4.94 g. (0.015 mol.) of carbon tetrabromide, 3.90 g. (0.015 mol.) of triphenylphosphine and 0.975 g. (0.015 g.-atom) of zinc in 25 ml. of carbon tetrachloride is stirred at 25° for 24 hours. A solution of 1.0 g. (7.45 mmol.) of p-ethylbenzaldehyde in 10 ml. of methylene chloride is added and the reaction mixture is stirred an additional two hours. Petroleum ether (140 ml.) is added to the mixture, the organic layer is decanted and the residue is extracted with 1:4 methylene chloride-petroleum ether. The combined organic solutions are concentrated under reduced pressure to give 1,1-dibromo-2-(4-ethylphenyl)ethylene.

1,1-Dibromo-2-(4-ethylphenyl)ethylene (1.1 g., 3.69 mmol.) is dissolved in 20 ml. of dry tetrahydrofuran and maintained under a nitrogen atmosphere. The solution is cooled to −78° and 3.9 ml. of a 1.9 M solution of butyl lithium in hexane is added with stirring. The reaction mixture is stirred one hour at −78°, then warmed to ambient temperature and stirred an additional hour. Water is added, the mixture is extracted with petroleum ether, the extracts are combined, dried (MgSO$_4$) and concentrated to give 4-ethylphenylacetylene.

To a cooled (0°) solution of 10.5 g. of cupric sulfate in 40 ml. of 28% ammonium hydroxide and 160 ml. of water is added under a nitrogen atmosphere 5.58 g. (0.08 mol.) of hydroxylamine hydrochloride. A solution of 5.2 g. (0.04 mol.) of 4-ethylphenylacetylene in 200 ml. of ethanol is then added and the reaction mixture is stirred for 15 minutes. The mixture is allowed to warm to ambient temperature and the precipitate is collected by filtration and washed with water, ethanol and ether to give cuprous 4-ethylphenylacetylide.

A flask containing 5.4 g. (0.028 mol.) of cuprous 4-ethylphenylacetylide in 100 ml. of pyridine is thoroughly flushed with nitrogen. A solution of 6.19 g. (0.028 mol.) of o-iodophenol in 50 ml. of pyridine is added under nitrogen and the reaction mixture is stirred and heated at 120° for 22 hours. The pyridine is removed by distillation in vacuo, the residue is added to an ice-water mixture and the gummy precipitate is collected and dissolved in methylene chloride. The methylene chloride solution is washed with 3N hydrochloric acid and water and concentrated under reduced pressure to give a residue which is chromatographed on a silica gel "dry-column" to give 2-(4-ethylphenyl)benzofuran.

Acylation of 2-(4-ethylphenyl)benzofuran with p-anisoyl chloride followed by demethylation of the product methoxybenzoyl compound and reaction of the hydroxylbenzoyl benzofuran thus formed with N-t-butyl-3-chloromethylazetidine as previously described gives the title compound.

EXAMPLE 24

When a substituted benzaldehyde listed below:

p-fluorobenzaldehyde
p-t-butylbenzaldehyde
p-propoxybenzaldehyde
α,α,α-trifluoro-p-tolualdehyde is used as a starting material in the procedure of Example 23 in place of p-ethylbenzaldehyde, the product phenylacetylenes are converted to the corresponding cuprous phenylacetylides and the cuprous phenylacetylides are reacted with o-iodophenol as described therein, the following benzofurans are obtained, respectively:

2-(4-fluorophenyl)benzofuran
2-(4-t-butylphenyl)benzofuran
2-(4-propoxyphenyl)benzofuran
2-(4-trifluoromethylphenyl)benzofuran.

Acylation of a 2-substituted benzofuran listed above with 4-(N-t-butyl-3-azetidinomethoxy)benzoyl chloride as described above gives the compounds of this invention listed below:

3-[4-(N-t-butyl-3-azetidinomethoxy)benzoyl]-2-(4-fluorophenyl)benzofuran
3-[4-(N-t-butyl-3-azetidinomethoxy)benzoyl]-2-(4-t-butylphenyl)benzofuran
3-[4-(N-t-butyl-3-azetidinomethoxy)benzoyl]-2-(4-propoxyphenyl)benzofuran
3-[4-(N-t-butyl-3-azetidinomethoxy)benzoyl]-2-(4-trifluoromethylphenyl)benzofuran.

EXAMPLE 25

3-[4-(N-t-Butyl-3-azetidinomethoxy)benzoyl]-2-phenylbenzothiophene

To a slurry of 4.0 g. (0.03 mol.) of anhydrous aluminum chloride in 30 ml. of carbon disulfide under a nitrogen atmosphere at 5° is added a mixture of 2.1 g. (0.01 mol.) of 2-phenylthiophene in 40 ml. of 1:1 carbon disulfide-methylene chloride containing an equimolar amount of 4-(N-t-butyl-3-azetidinomethoxy)- benzoyl chloride. After addition, the reaction mixture is warmed to ambient temperature and stirred for 16 hours. Dilute aqueous hydrochloric acid is added to the mixture and the layers are separated. The aqueous phase is re-extracted with chloroform and the organic layers are combined and concentrated to give the title compound as a residue which, when treated with ethereal hydrochloric acid and chromatographed on silica gel with methanol-chloroform as eluant, gives the title compound as the corresponding hydrochloride salt.

EXAMPLE 26

When an equivalent amount of a benzothiophene listed below:

3-phenylbenzothiophene
2-benzylbenzothiophene
5-chloro-3-phenylbenzothiophene
2-(4-methoxyphenyl)benzothiophene is used as a starting material in the procedure of Example 25 in place of 2-phenylbenzothiophene, the following compounds of this invention are obtained and isolated as the corresponding hydrochloride salts:

2-[4-(N-t-butyl-3-azetidinomethoxy)benzoyl]-3-phenylbenzothiophene
2-benzyl-3-[4-(N-t-butyl-3-azetidinomethoxy)-benzoyl]benzothiophene
2-[4(N-t-butyl-3-azetidinomethoxy)benzoyl]-5-chloro-3-phenylbenzothiophene
3-[4-(N-t-butyl-3-azetidinomethoxy)benzoyl]-2-(4-methoxyphenyl)benzothiophene.

EXAMPLE 27

Addition of an ethereal solution of oxalic acid to a solution of 3-[4-(N-t-butyl-3-azetidinomethoxy)-benzoyl]-2-phenylbenzofuran in ether gives the oxalate salt.

The corresponding hydrochloride salt may be prepared from the oxalate salt by passage of a solution of 3-[4-(N-t-butyl-3-azetidinomethoxy)benzoyl]-2-phenylbenzofuran oxalate in ethanol through an Amberlite IRA-401 chloride ion exchange column.

In a similar manner, other acid addition salts may be prepared.

EXAMPLE 28

| Ingredients | Amounts |
|---|---|
| 3-[4-(N-t-butyl-3-azetidinomethoxy)-benzoyl]-2-phenylbenzofuran | 100 mg. |
| Calcium sulfate dihydrate | 150 mg. |
| Sucrose | 25 mg. |
| Starch | 15 mg. |
| Talc | 5 mg. |
| Stearic acid | 3 mg. |

The sucrose, calcium sulfate dihydrate and 3-[4-(N-t-butyl-3-azetidinomethoxy)benzoyl]-2-phenylbenzofuran are thoroughly mixed and granulated with 10% gelatin solution. The wet granules are screened, dried and then mixed with the starch, talc and stearic acid, screened and compressed into a tablet.

EXAMPLE 29

| Ingredients | Amounts |
|---|---|
| 3-[4-(N-t-butyl-3-azetidinomethoxy)benzoyl]-2-phenyl-benzofuran | 150 mg. |
| Magnesium stearate | 5 mg. |
| Lactose | 100 mg. |

The ingredients are mixed and filled into a hard gelatin capsule.

Similarly, the other substituted benzofurans disclosed herein may be formulated into tablets and capsules by the procedures of Examples 28 and 29.

The compositions prepared as in Examples 28 and 29 are administered orally to a subject in need of coronary vasodilator activity within the dose ranges given hereabove.

What is claimed is:

1. A compound of the formula:

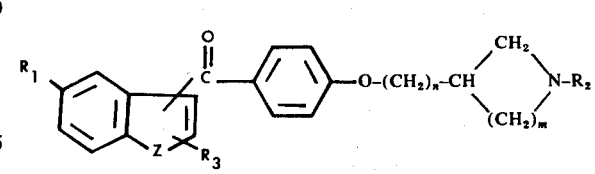

or a pharmaceutically acceptable acid addition salt thereof, in which:

$R_1$ is hydrogen, chloro, bromo, trifluoromethyl or lower alkyl;

$R_2$ is straight or branched chain alkyl of from one to six carbon atoms;

$R_3$ is lower alkyl or phenyl$(CH_2)_p$ where $p$ is 0 or 1 and the phenyl moiety is unsubstituted or substituted in the para-position with lower alkyl, lower alkoxy, halogen or trifluoromethyl;

$m$ is 1 to 4;

$n$ is 0 or 1; and

Z is oxygen or sulfur.

2. A compound according to claim 1 in which Z is oxygen.

3. A compound according to claim 2 in which $R_3$ is in the 2-position of the benzofuran nucleus.

4. A compound according to claim 3 in which $R_1$ is hydrogen and $R_3$ is phenyl or phenyl substituted in the para-position with lower alkyl, lower alkoxy, halogen or trifluoromethyl.

5. A compound according to claim 4 in which $R_3$ is phenyl.

6. A compound according to claim 5 in which $R_2$ is branched chain alkyl of from three to six carbon atoms.

7. A compound according to claim 6, said compound having the formula:

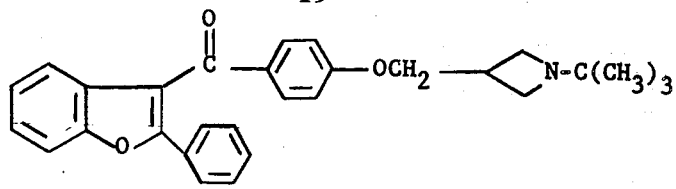

8. A pharmaceutical composition having coronary vasodilator activity comprising a pharmaceutical carrier and an effective amount of a compound of claim 1.

9. A method of producing coronary vasolidation in an animal in need thereof comprising administering to said animal an effective amount of a compound of claim 1.

10. A pharmaceutical composition having anti-anginal activity comprising a pharmaceutical carrier and an effective amount of the compound of claim 7.

11. A method of producing anti-anginal activity in an animal in need thereof comprising administering to said animal an effective amount of the compound of claim 7.

* * * * *